(12) United States Patent
Mizoguchi et al.

(10) Patent No.: US 10,390,688 B2
(45) Date of Patent: Aug. 27, 2019

(54) IMAGE PICKUP SYSTEM

(71) Applicant: OLYMPUS CORPORATION, Tokyo (JP)

(72) Inventors: Masakazu Mizoguchi, Hachioji (JP); Satoshi Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 321 days.

(21) Appl. No.: 15/474,172

(22) Filed: Mar. 30, 2017

(65) Prior Publication Data

US 2017/0202441 A1 Jul. 20, 2017

Related U.S. Application Data

(63) Continuation of application No. PCT/JP2015/081359, filed on Nov. 6, 2015.

(30) Foreign Application Priority Data

Nov. 21, 2014 (JP) .................. 2014-236898

(51) Int. Cl.
*A61B 1/045* (2006.01)
*G01B 11/00* (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
CPC .................................................. A61B 1/045
See application file for complete search history.

(56) References Cited

U.S. PATENT DOCUMENTS 9,782,056 B2 * 10/2017 McDowall ......... G02B 27/0075
10,254,533 B2 * 4/2019 McDowall ......... G02B 23/2415
(Continued)

FOREIGN PATENT DOCUMENTS

JP H05-076486 A 3/1993
JP H06-265796 A 9/1994
(Continued)

OTHER PUBLICATIONS

International Search Report dated Jan. 26, 2016 issued in PCT/JP2015/081359.

*Primary Examiner* — Rowina J Cattungal
(74) *Attorney, Agent, or Firm* — Scully, Scott, Murphy & Presser P.C.

(57) ABSTRACT

An image pickup system includes a stereoscopic endoscope including image pickup optical systems having a parallax therebetween and a first image pickup device and a second image pickup device, and a processor including a first photometric measurement section configured to photometrically measure a luminance value of a first image pickup signal related to the first image pickup device, a second photometric measurement section configured to measure a luminance value of a second image pickup signal related to the second image pickup device, and a control section including a threshold value comparison section configured to compare the luminance value with a threshold value. When the luminance value of either one of the first image pickup signal and the second image pickup signal exceeds the threshold value, the image pickup system performs light adjustment control of a light source based on a photometric value of the other image pickup signal.

6 Claims, 11 Drawing Sheets

(51) Int. Cl.
     *G03B 35/10*    (2006.01)
     *H04N 13/254*   (2018.01)
     *H04N 13/289*   (2018.01)
     *A61B 1/00*     (2006.01)
     *A61B 1/06*     (2006.01)
     *G01J 1/42*     (2006.01)
     *G02B 23/24*    (2006.01)
     *H04N 5/235*    (2006.01)
     *H04N 5/238*    (2006.01)
     *G03B 7/17*     (2014.01)
     *H04N 13/296*   (2018.01)
     *H04N 13/239*   (2018.01)
     *G03B 37/00*    (2006.01)
     *H04N 5/225*    (2006.01)

(52) U.S. Cl.
     CPC ........ *A61B 1/00193* (2013.01); *A61B 1/0661* (2013.01); *G01B 11/00* (2013.01); *G01J 1/4209* (2013.01); *G02B 23/2415* (2013.01); *G02B 23/2484* (2013.01); *G03B 7/17* (2015.01); *G03B 35/10* (2013.01); *H04N 5/238* (2013.01); *H04N 5/2351* (2013.01); *H04N 5/2353* (2013.01); *H04N 13/239* (2018.05); *H04N 13/254* (2018.05); *H04N 13/289* (2018.05); *H04N 13/296* (2018.05); *G03B 37/005* (2013.01); *H04N 2005/2255* (2013.01)

(56)  References Cited

U.S. PATENT DOCUMENTS

| | | | |
|---|---|---|---|
| 2013/0038689 | A1  | 2/2013 | McDowall |
| 2013/0041221 | A1* | 2/2013 | McDowall ......... A61B 1/00096 600/111 |
| 2014/0063201 | A1  | 3/2014 | Ohkoba |
| 2014/0092215 | A1* | 4/2014 | Hayama ............ A61B 1/00009 348/45 |

FOREIGN PATENT DOCUMENTS

| | | |
|---|---|---|
| JP | 2716936 B2       | 2/1998 |
| JP | 2001-148865 A    | 5/2001 |
| JP | 2008-048269 A    | 2/2008 |
| JP | 2012-065204 A    | 3/2012 |
| JP | 4955840 B2       | 6/2012 |
| JP | 2014-045800 A    | 3/2014 |
| JP | 2014-073143 A    | 4/2014 |
| JP | 2014-524290 A    | 9/2014 |
| WO | WO 2013/025530 A1 | 2/2013 |

\* cited by examiner

IMAGE PICKUP SYSTEM

CROSS REFERENCE TO RELATED APPLICATION

This application is a continuation application of PCT/JP2015/081359 filed on Nov. 6, 2015 and claims benefit of Japanese Application No. 2014-236898 filed in Japan on Nov. 21, 2014, the entire contents of which are incorporated herein by this reference.

BACKGROUND OF THE INVENTION

1. Field of the Invention

The present invention relates to an image pickup system, and particularly to an image pickup system capable of acquiring two picked-up images having a parallax therebetween.

2. Description of the Related Art

Conventionally, there has been known an image pickup system capable of acquiring two picked-up images having a parallax therebetween, e.g., an image pickup system which generates a stereoscopic image using two picked-up images having a parallax therebetween.

More specifically, Japanese Patent Application Laid-Open Publication No. 2012-065204 and Japanese Patent Application Laid-Open Publication No. 2001-148865 each disclose an image pickup apparatus which picks up a stereoscopic image (three-dimensional (3D) image) using a plurality of image pickup sections. The image pickup apparatus according to each of Japanese Patent Application Laid-Open Publication No. 2012-065204 and Japanese Patent Application Laid-Open Publication No. 2001-148865 photometrically measures an image pickup signal outputted from each of two image pickup sections and controls an exposure amount of the image pickup section based on a result of the photometric measurement (a luminance value).

For example, the image pickup apparatus according to Japanese Patent Application Laid-Open Publication No. 2012-065204 controls an image pickup exposure time related to each of the two image pickup sections so that luminance values of the image pickup signals respectively outputted from the image pickup sections are made equal to each other.

On the other hand, Japanese Patent No. 4955840 discloses a stereoscopic endoscope which generates a stereoscopic image using two picked-up images having a parallax therebetween to stereoscopically observe a fine operative site in a surgical operation of a body cavity. The stereoscopic endoscope includes a pair of left and right observation optical systems and a pair of left and right image pickup sections respectively corresponding to the observation optical systems.

Japanese Patent No. 2716936 discloses a stereoscopic endoscope which synthesizes respective left and right image signals from two image pickup devices into one system and performs image processing using one camera control unit.

SUMMARY OF THE INVENTION

According to an aspect of the present invention, there is provided an image pickup system including a light source configured to irradiate an object with illumination light, a first image pickup section including a first image pickup device capable of picking up an optical image of the object and outputting the optical image as a first image pickup signal, a second image pickup section including a second image pickup device capable of picking up the optical image of the object and outputting the optical image as a second image pickup signal having a parallax from the first image pickup signal, a first photometric measurement section configured to detect a brightness of an object image as a first photometric value for the first image pickup signal, a second photometric measurement section configured to detect a brightness of the object image as a second photometric value for the second image pickup signal, a first exposure time control section configured to control an exposure time of the first image pickup signal based on the first photometric value, a second exposure time control section configured to control an exposure time of the second image pickup signal based on the second photometric value, an exposure control section configured to control at least one of the first exposure time control section and the second exposure time control section so that the brightness of the object image for the first image pickup signal and the brightness of the object image for the second image pickup signal become equal to each other, a photometric value selection section configured to select either one of the first photometric value detected in the first photometric measurement section and the second photometric value detected in the second photometric measurement section, and a light amount control section configured to control a light amount of the illumination light irradiated from the light source based on the first photometric value or the second photometric value selected by the photometric value selection section.

DETAILED DESCRIPTION OF THE PREFERRED EMBODIMENTS

Embodiments of the present invention will be described below with reference to the drawings.

First Embodiment

Figure 1:
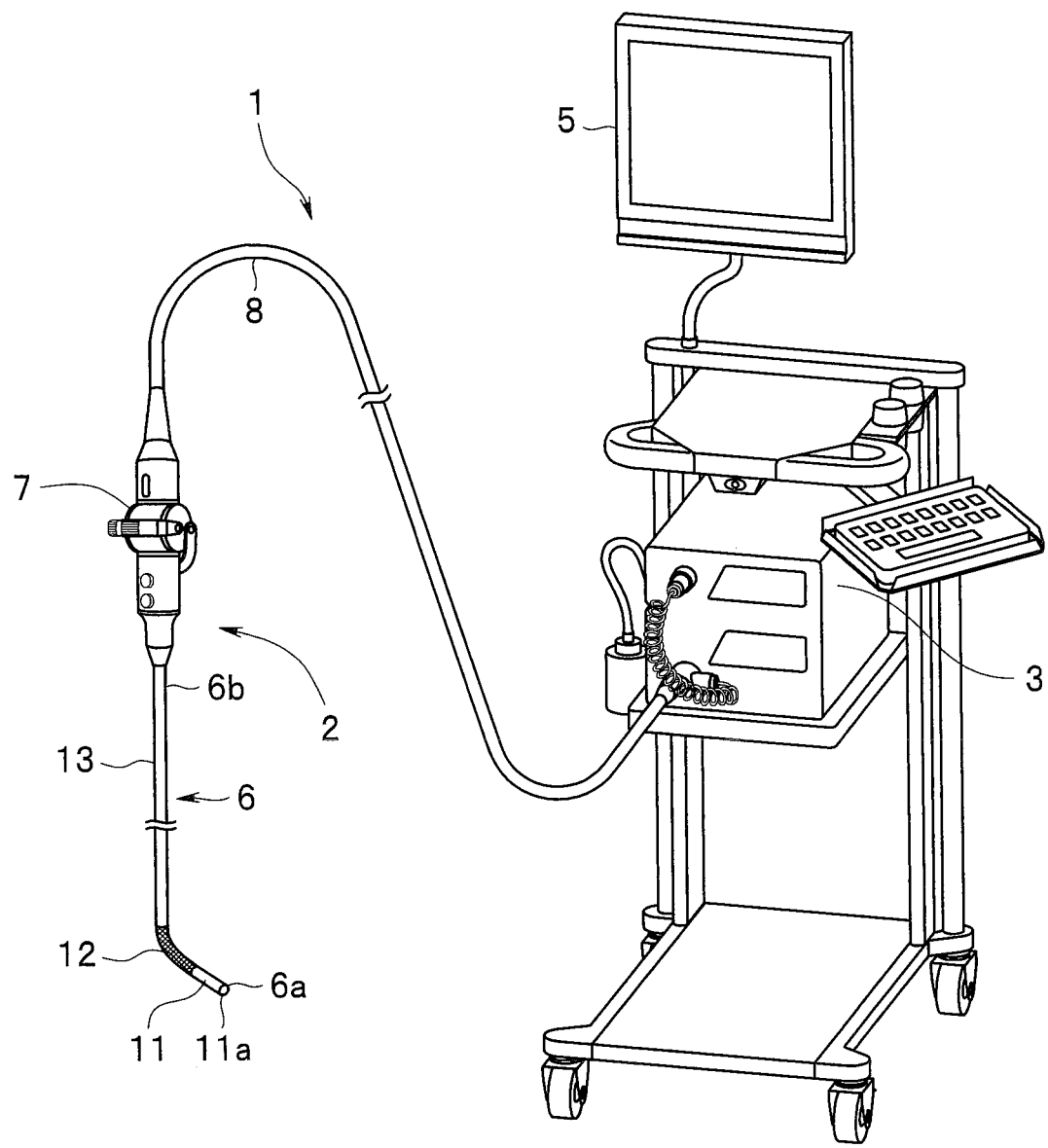
FIG. 1 is an external perspective view illustrating an entire configuration of an endoscope system according to a first embodiment of the present invention.
Figure 2:
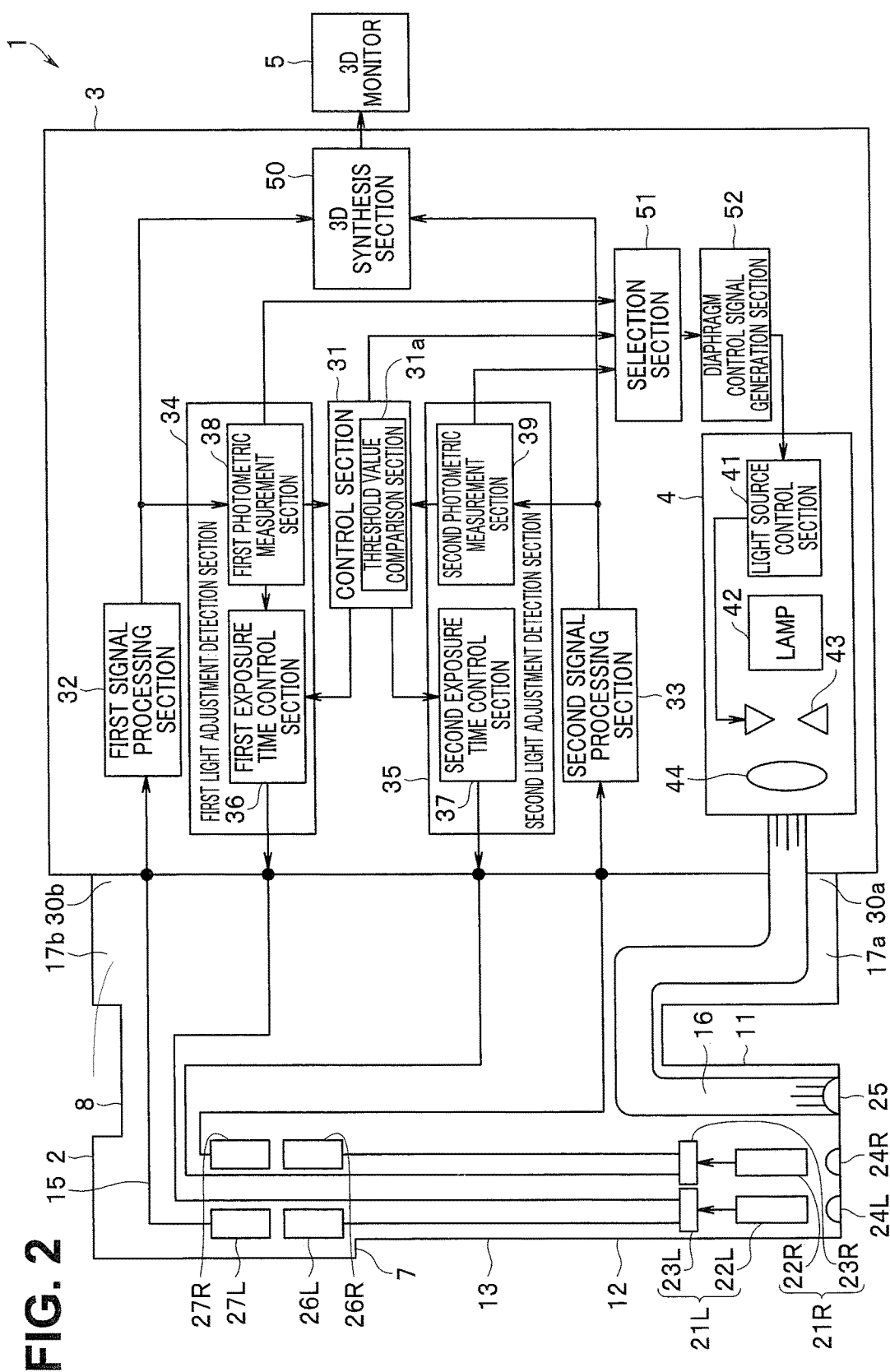
FIG. 2 is a block diagram illustrating a configuration of the endoscope system according to the first embodiment.
Figure 3:
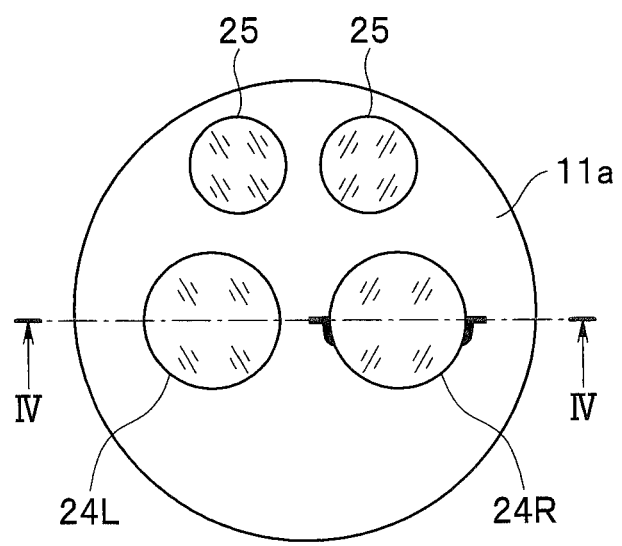
FIG. 3 is a front view of a distal end portion of an insertion section in an endoscope in the endoscope system according to the first embodiment.
Figure 4:
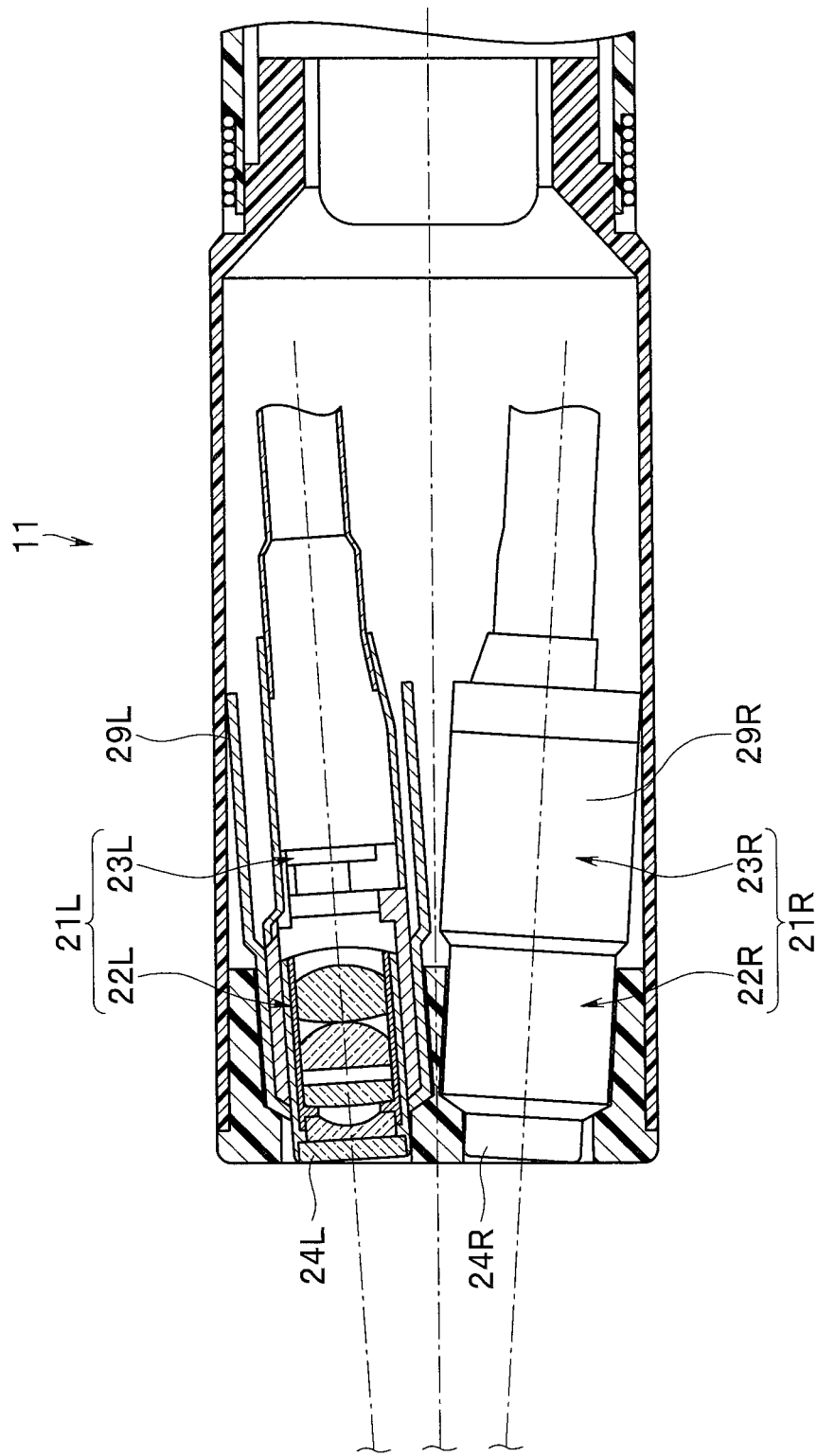
FIG. 4 is a cross-sectional view of the distal end portion of the insertion section in the endoscope in the endoscope system according to the first embodiment.

A configuration of an endoscope system according to a first embodiment will be described with reference to FIGS. 1 to 4. FIG. 1 is an external perspective view illustrating an entire configuration of the endoscope system according to the first embodiment of the present invention, FIG. 2 is a block diagram illustrating a configuration of the endoscope system according to the first embodiment, FIG. 3 is a front view of a distal end portion of an insertion section in an endoscope in the endoscope system according to the first embodiment, and FIG. 4 is a cross-sectional view of the distal end portion of the insertion section in the endoscope in the endoscope system according to the first embodiment.

As illustrated in FIG. 1, an endoscope system 1 according to the first embodiment of the present invention includes, as its principal part, a stereoscopic endoscope 2 serving as a so-called 3D endoscope configured to generate a stereoscopic image using two image pickup units having a parallax therebetween, a processor 3, to which the stereoscopic endoscope 2 is detachably connected, including a light source section configured to perform predetermined signal processing for respective image pickup signals from the image pickup units while supplying illumination light to the stereoscopic endoscope 2, and a monitor 5 serving as a display device configured to display an image signal generated by the processor 3 as an endoscope image.

In the present embodiment, the stereoscopic endoscope 2 is a rigid endoscope applied to an abdominal procedure, for example, for stereoscopically observing an operative site in a body cavity. The stereoscopic endoscope 2 includes a rigid insertion section 6 to be inserted into the body cavity and having a length applied to the abdominal procedure, an operation section 7 gripped by an operator and configured to perform various operations of the stereoscopic endoscope 2, and a universal cord 8 extending from the insertion section 7 and connected to the processor 3.

The insertion section 6 includes a distal end rigid portion 11, a bending portion 12, and a rigid portion 13 connected in this order from a distal end portion 6a toward a proximal end portion 6b. That is, a proximal end portion of the distal end rigid portion 11 is connected to a distal end portion of the bending portion 12, and a proximal end portion of the bending portion 12 is connected to a distal end portion of the rigid portion 13. The above-described rigid portion 13 is a rigid tube, which is elongated and rigid, and a proximal end portion of the rigid portion 13 is connected to the operation section 7 as the proximal end portion 6b in the insertion section 6.

As illustrated in FIGS. 2, 3, and 4, a left-side image pickup unit 21L for a left-side image (left eye) and a right-side image pickup unit 21R for a right-side image (right eye) are disposed to stereoscopically observe the operative site in the distal end rigid portion 11 in the insertion section 6.

The above-described left-side image pickup unit 21L includes an image pickup optical system 22L and an image pickup device 23L for a left-side image (left eye), and the above-described right-side image pickup unit 21R includes an image pickup optical system 22R and an image pickup device 23R for a right-side image (right eye).

As illustrated in FIG. 4, each of the image pickup optical system 22L for a left-side image and the image pickup optical system 22R for a right-side image includes an objective lens for observing an operative site and an image forming lens for forming an image of the operative site observed by the objective lens.

Furthermore, the image pickup device 23L and the image pickup device 23R are respectively disposed at respective image forming positions of the image forming lenses in the image pickup optical system 22L and the image pickup optical system 22R. The image pickup device 23L and the image pickup device 23R respectively include CCD (charge coupled device) image sensors, for example, and pass through the objective lenses in the image pickup optical system 22L and the image pickup optical system 22R and photoelectrically convert images (operative sites) formed by the image forming lenses to generate predetermined image pickup signals.

Correlated double sampling circuits (hereinafter referred to as CDS circuits) 26L and 26R and analog-digital conversion circuits (hereinafter referred to as A/D conversion circuits) 27L and 27R are respectively provided in subsequent stages of the image pickup device 23L and the image pickup device 23R.

The image pickup device 23L and the image pickup device 23R respectively photoelectrically convert object images formed on their image pickup surfaces and output the object images to the CDS circuits 26L and 26R. The CDS circuits 26L and 26R respectively subject image pickup signals to correlated double sampling processing and output the image pickup signals to the A/D conversion circuits 27L and 27R. The A/D conversion circuits 27L and 27R respectively convert the image pickup signals from analog signals to digital signals and output the image pickup signals to the processor 3.

On the other hand, various types of cables 15 such as signal lines related to the image pickup device 23L and the image pickup device 23R are connected to the processor 3 via the insides of the insertion section 6, the operation section 7, and the universal cord 8. A light guide cable 16 configured to transmit illumination light from the light source section in the processor 3 is inserted through the insertion section 6, the operation section 7, and the universal cord 8.

On the side of a proximal end of the universal cord 8, a light source connector 17a serving as an end of the light guide cable 16 is disposed, and is detachably connected to a light source connector section 30a in the processor 3. On the other hand, a signal connector 17b branched from the light source connector 17a and serving as an end of the signal cable 15 is disposed, and is detachably connected to a signal connector section 30b in the processor 3.

As illustrated in FIG. 3, an illumination window 25 is disposed at a position opposing a distal end surface of the light guide cable 16 on a distal end surface 11a of the distal end rigid portion 11 in the insertion section 6. Note that the light guide cable 16 includes two light guide cables 16 and the illumination window 25 also includes two illumination windows 25 in the present embodiment.

The light source connector 17a is connected to the light source connector section 30a in the processor 3, illumination light emitted from the light source section 4 internally provided in the processor 3 is transmitted with the light guide cable 16, and the illumination light is emitted from the illumination window 25 provided to oppose the distal end surface of the light guide cable 16 on the distal end surface 11a of the distal end rigid portion 11.

On the other hand, on the distal end surface 11a of the distal end rigid portion 11, two observation windows 24L and 24R are disposed adjacent to the illumination window 25, and an optical image of an object such as an illuminated affected site is inputted thereto. Note that the observation windows 24L and 24R are respectively arranged at positions opposing the image pickup optical system 22L and the image pickup optical system 22R, described above.

As illustrated in FIG. 4, the stereoscopic endoscope 2 includes a left-side accommodating section 29L accommodating the left-side image pickup unit 21L and a right-side accommodating section 29R accommodating the right-side image pickup unit 21R. Note that the accommodating section 29L and the accommodating section 29R are respectively separate sections.

Note that, in the present embodiment as described above, while the optical images having a parallax therebetween are respectively inputted in the two left and right image pickup optical systems 22L and 22R as a 3D endoscope, a left-side optical image and a right-side optical image respectively serving as separate optical images are generated, and the separate left and right optical images are respectively photoelectrically converted in the separate image pickup devices 23L and 23R, the present invention is not limited to this.

That is, one image pickup device may be arranged at the respective image forming positions of the image forming lenses in the image pickup optical system 22L and the image pickup optical system 22R, and the separate left and right optical images may be respectively formed in different regions on the same image pickup surface of the one image pickup device.

In this case, in the processor 3 configured to process an image pickup signal outputted from the one image pickup device, image pickup signals related to the different regions on the same image pickup surface may be respectively processed as the left and right optical images.

While a CCD image sensor has been adopted as the image pickup device 23L and the image pickup device 23R in the present embodiment, the present invention is not limited to this. For example, an image sensor such as a CMOS may be used.

The processor 3 in the endoscope system according to the first embodiment will be described in detail below.

As illustrated in FIG. 2, the processor 3 in the present embodiment includes a control section 31 configured to control various types of circuits in the processor 3, a first signal processing section 32 configured to receive, out of two image pickup signals in the stereoscopic endoscope 2, an image pickup signal (hereinafter referred to as a first image pickup signal), which has been generated in the image pickup device 23L for a left-side image and has passed through the CDS circuit 26L and the A/D conversion circuit 27L, and subject the first image pickup signal to predetermined signal processing under the control of the control section 31, and a second signal processing section 33 configured to receive an image pickup signal (hereinafter referred to as a second image pickup signal), which has been generated in the image pickup device 23R for a right-side image and has passed through the CDS circuit 26R and the A/D conversion circuit 27R, and subject the second image pickup signal to predetermined signal processing under the control of the control section 31.

The control section 31 includes a threshold value comparison section 31a configured to compare a luminance value of the first image pickup signal or the second image pickup signal, which has been processed in the first signal processing section 32 or the second signal processing section 33, with a predetermined threshold value.

While both the first signal processing section 32 and the second signal processing section 33 respectively subject the image pickup signals from the image pickup device 23L and the image pickup device 23R to the predetermined signal processing, each of the first and second signal processing sections 32 and 33 includes known signal processing sections such as an automatic gain control circuit (AGC circuit), a white balance circuit, a gamma correction circuit, a scaling circuit, and a contour enhancement circuit, and performs signal processing, as needed.

Referring to FIG. 2 again, the processor 3 includes a first light adjustment detection section 34 configured to detect light adjustment of the first image pickup signal processed in the first signal processing section 32, a second light adjustment detection section 35 configured to detect light adjustment of the second image pickup signal processed in the second signal processing section 33, and a 3D synthesis section 50 configured to synthesize the first image pickup signal processed in the first signal processing section 32 and the second image pickup signal processed in the second signal processing section 33 to generate a predetermined 3D image signal.

The first light adjustment detection section 34 includes a first photometric measurement section 38 configured to photometrically measure the luminance of the first image pickup signal processed in the first signal processing section 32 and output an information signal (first photometric value signal) related to a first photometric value (first luminance value), and a first exposure time control section 36 configured to output a first exposure control signal for controlling an exposure time to the image pickup device 23L in response to the first luminance value obtained by the photometric measurement in the first photometric measurement section 38.

On the other hand, the second light adjustment detection section 35 includes a second photometric measurement section 39 configured to photometrically measure the luminance of the second image pickup signal processed in the second signal processing section 33 and output an information signal (second photometric value signal) related to a second photometric value (second luminance value), and a second exposure time control section 37 configured to output a second exposure control signal for controlling an exposure time to the image pickup device 23R in response to the second luminance value obtained by the photometric measurement in the second photometric measurement section 39.

The first exposure time control section 36 generates a control signal for electronic shutter control of the image pickup device 23L in response to the first photometric value obtained by photometrically measuring the luminance of the first image pickup signal, and sends out the generated control signal to the image pickup device 23L. On the other hand, the second exposure time control section 37 generates a control signal for electronic shutter control of the image pickup device 23R in response to the second photometric value obtained by photometrically measuring the luminance of the second image pickup signal, and sends out the generated control signal to the image pickup device 23R.

Furthermore, the processor 3 includes a photometric value signal selection section 51 configured to select either one of the first photometric value signal from the first photometric measurement section 38 and the second photometric value signal from the second photometric measurement section 39 under the control of the control section 31, and a diaphragm control signal generation section 52 configured to generate a diaphragm control signal in response to the first photometric value signal or the second photometric value signal selected in the photometric value signal selection section 51.

Note that the photometric value signal selection section 51 is set to select the first photometric value signal from the first photometric measurement section 38 in an initial state in the present embodiment.

In the present embodiment, the processor 3 is internally provided with the light source section 4 for emitting illumination light to the light guide cable 16 to supply illumination light to the stereoscopic endoscope 2.

The light source section 4 is configured to include a lamp 42, a diaphragm 43, and a lens 44 while including a light source control section 41. Illumination light from the lamp 42 is emitted toward the lens 44 via the diaphragm 43 controlled by the light source control section 41. The lens 44 collects light at a proximal end portion of the light guide cable 16.

Furthermore, the light collected at the proximal end portion of the light guide cable 16 is emitted from a distal end portion of the light guide cable 16 after being transmitted through the light guide cable 16 as illumination light to be supplied to the stereoscopic endoscope 2.

The light source control section 41 controls the diaphragm 43 based on the diaphragm control signal generated in the diaphragm control signal generation section 52.

That is, in the first embodiment, the light source control section 41 controls the diaphragm 43 to control a light amount of illumination light based on the diaphragm control signal generated in response to the first photometric value signal or the second photometric value signal selected in the photometric value signal selection section 51.

Thus, in the endoscope system according to the first embodiment, the first light adjustment detection section 34 and the second light adjustment detection section 35 respectively individually control the exposure time of the image pickup signal for the image pickup device 23L and the image pickup device 23R, and perform control so that the luminance values of the first image pickup signal and the second image pickup signal become equal to each other, as described above.

On the other hand, the endoscope system according to the present embodiment respectively generates the diaphragm control signals in the photometric value signal selection section 51 and the diaphragm control signal generation section 52 in response to the first photometric value signal and the second photometric value signal respectively detected in the first photometric measurement section 38 and the second photometric measurement section 39 in the first light adjustment detection section 34 and the second light adjustment detection section 35, and thus performs light adjustment of the light source by controlling the diaphragm 43 in the light source section 4.

Light Adjustment Control of Light Source

Light adjustment control of the light source in the present embodiment will be described below.

The control section 31 in the processor 3 includes the threshold value comparison section 31a configured to compare the luminance value of the first image pickup signal or the second image pickup signal with the predetermined threshold value, as described above. The threshold value comparison section 31a always compares the respective luminance values of the first image pickup signal and the second image pickup signal obtained by the photometric measurement in the first photometric measurement section 38 in the first light adjustment detection section 34 and the second photometric measurement section 39 in the second light adjustment detection section 35 with the predetermined threshold value.

The control section 31 issues an instruction to change or maintain the first photometric value signal (or the second photometric value signal) selected by controlling the photometric value signal selection section 51 when the luminance value of the first image pickup signal or the second image pickup signal is higher or lower than the predetermined threshold value in the threshold value comparison section 31a.

For example, while the photometric value signal selection section 51 is set to select the first photometric value signal in the initial state in the present embodiment, as described above, the control section 31 instructs the photometric value signal selection section 51 to select the second photometric value signal depending on a detection result in the threshold value comparison section 31a.

More specifically, if the luminance value of the first image pickup signal obtained by the photometric measurement in the first photometric measurement section 38 reaches not less than the predetermined threshold value and the luminance value of the second image pickup signal obtained by the photometric measurement in the second photometric measurement section 39 is less than the predetermined threshold value by the detection in the threshold value comparison section 31a, the control section 31 instructs the photometric value signal selection section 51 to select the second photometric value signal instead of the first photometric value signal.

On the other hand, if the luminance value of the first image pickup signal obtained by the photometric measurement in the first photometric measurement section 38 reaches less than the predetermined threshold value and if the luminance value of the first image pickup signal is not less than the predetermined threshold value and the luminance value of the second image pickup signal is also not less than the predetermined threshold value while the second photometric value signal is selected in the photometric value signal selection section 51, the photometric value signal selection section 51 is instructed to select the first photometric value signal instead of the second photometric value signal.

Note that, if the luminance value of the first image pickup signal is not less than the predetermined threshold value and the luminance value of the second image pickup signal is also not less than the predetermined threshold value while the first photometric value signal is selected in the photometric value signal selection section 51, the photometric value signal selection section 51 is instructed to maintain the selection of the first photometric value signal as it is.

The following is assumed as a case where the luminance value of the first image pickup signal or the second image pickup signal exceeds the predetermined threshold value.

The stereoscopic endoscope 2 in the endoscope system according to the invention of the application assumes the rigid endoscope applied to the abdominal procedure, as described above. In the abdominal procedure, a predetermined treatment instrument such as forceps, together with the rigid endoscope, can also be used.

In the case of the abdominal procedure thus also using the treatment instrument such as the forceps, when the treatment instrument such as the forceps enters a field of view range related to either one of left and right image pickup optical systems in the stereoscopic endoscope 2, illumination light is reflected on a surface of the forceps depending on an entrance status (an entrance angle, etc.) of the forceps. Thus, relatively intense and bright light may be incident on either one of the left and right image pickup optical systems. In such a case, the luminance value of the first image pickup signal or the second image pickup signal obtained by the photometric measurement in the first photometric measurement section 38 or the second photometric measurement section 39 may exceed the predetermined threshold value.

When the luminance value of the first image pickup signal or the second image pickup signal thus becomes so large as to exceed the predetermined threshold value, if any countermeasure is not taken, the diaphragm 43 in the light source section 4 rapidly changes in response to the diaphragm control signal generated in the diaphragm control signal generation section 52 in response to the luminance value, and the light amount of illumination light also greatly changes rapidly.

While the exposure times of the image pickup signals are respectively controlled for the image pickup device 23L and the image pickup device 23R, to perform control so that the respective luminance values of the first image pickup signal and the second image pickup signal become equal to each other in the present embodiment, as described above, the exposure times may not be accurately controlled when the light amount itself of illumination light greatly changes rapidly.

The invention of the application has been made in view of such circumstances, and is directed to providing an endoscope system capable of maintaining accurate exposure control of image pickup signals even if a treatment instrument such as forceps enters a field of view range related to either one of left and right image pickup optical systems in a stereoscopic endoscope 2 and relatively intense and bright light is incident on an image pickup section on the entrance side.

Function of First Embodiment

A function of the endoscope system according to the first embodiment will be described below.

Figure 5:
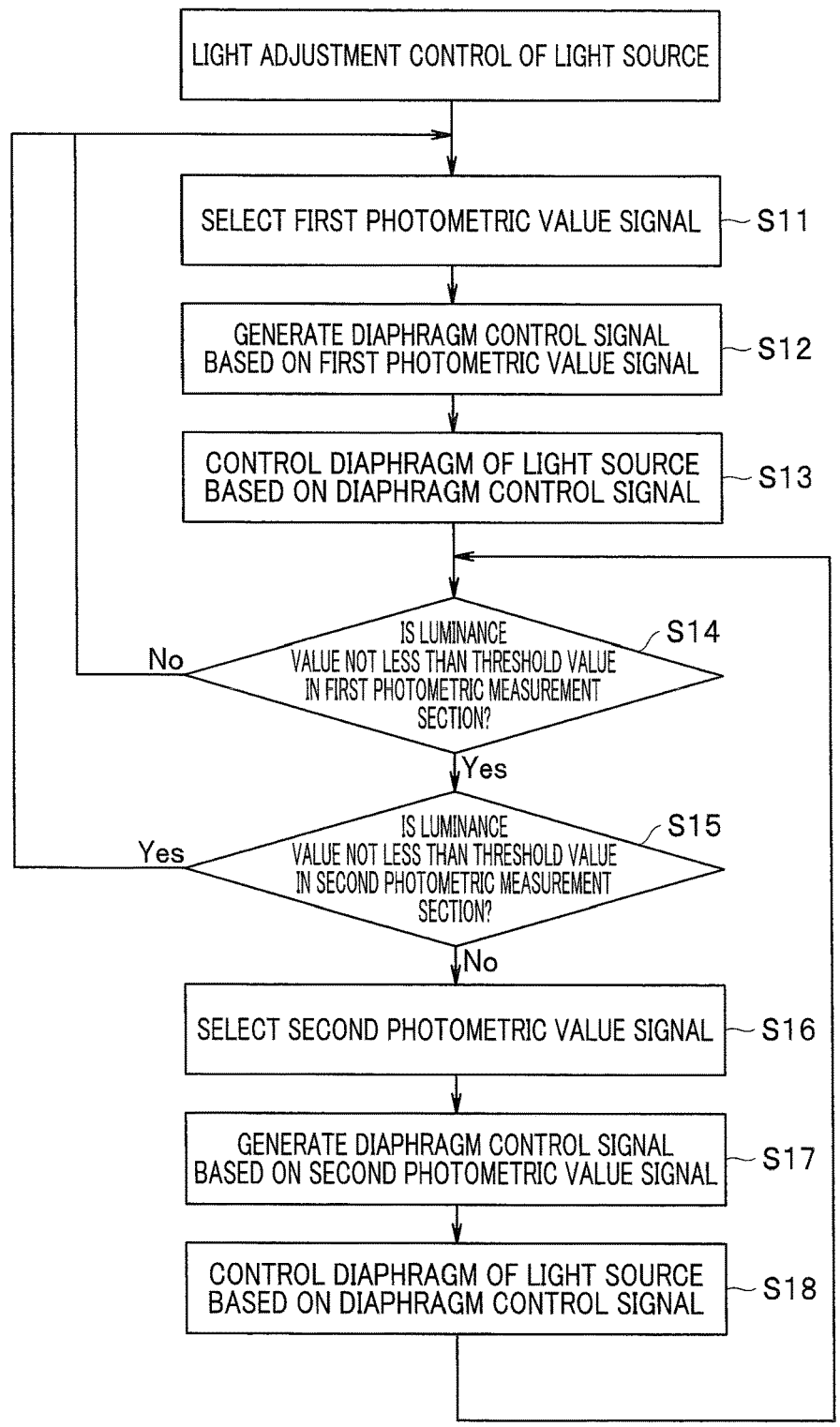
FIG. 5 is a flowchart illustrating light adjustment control of a light source in the case of a procedure in the endoscope system according to the first embodiment.

FIG. 5 is a flowchart illustrating the light adjustment control of the light source in the case of a procedure in the endoscope system according to the first embodiment.

When the control of the light source is started under the control of the control section 31 in the processor 3, the photometric value signal selection section 51 selects a first photometric value signal under the control of the control section 31 (step S11), and the diaphragm control signal generation section 52 then generates a diaphragm control signal based on the first photometric value signal (step S12). The light source control section 41 in the light source section 4 controls the diaphragm 43 based on the diaphragm control signal, which has been generated in step S12, under the control of the control section 31 (step S13).

On the other hand, a luminance value of a first image pickup signal and a luminance value of a second image pickup signal are respectively photometrically measured under the control of the control section 31 in the first photometric measurement section 38 in the first light adjustment detection section 34 and the second photometric measurement section 39 in the second light adjustment detection section 35.

The threshold value comparison section 31a in the control section 31 then compares the luminance value of the first image pickup signal with a predetermined threshold value, and determines whether the luminance value of the first image pickup signal is not less than the threshold value (step S14).

Unless the luminance value of the first image pickup signal reaches not less than the threshold value in step S14, the processing returns to step S11. In step S11, the control section 31 controls the photometric value signal selection section 51, the diaphragm control signal generation section 52, and the light source control section 41 so that the control of the diaphragm 43 based on the first photometric value signal is continued.

If the threshold value comparison section 31a determines that the luminance value of the first image pickup signal is not less than the threshold value, i.e., if the luminance value of the first image pickup signal reaches not less than the threshold value because the treatment instrument such as the forceps enters the field of view range of the image pickup device 23L out of the two left and right image pickup devices and relatively intense and bright light is incident on the field of view range in step S14, described above, the threshold value comparison section 31a then compares the luminance value of the second image pickup signal with the predetermined threshold value, and determines whether the luminance value of the second image pickup signal is not less than the threshold value (step S15).

If the threshold value comparison section 31a determines that the luminance value of the second image pickup signal is less than the threshold value, i.e., if relatively intense and bright light is incident on only the image pickup device 23L, the control section 31 instructs the photometric value signal selection section 51 to select the second photometric value signal instead of the first photometric value signal (step S16).

The diaphragm control signal generation section 52 generates a diaphragm control signal based on the second photometric value signal (step S17), and the light source control section 41 in the light source section 4 controls the diaphragm 43 based on the diaphragm control signal, which has been generated in step S17, under the control of the control section 31 (step S18).

The control section 31 instructs the photometric value signal selection section 51 to select the second photometric value signal instead of the first photometric value signal. Even while the second photometric value signal is selected, the threshold value comparison section 31a also continues to compare the luminance value of the first image pickup signal with the predetermined threshold value. If the luminance value of the first image pickup signal reaches less than the predetermined threshold value and if the luminance value of the first image pickup signal is not less than the predetermined threshold value and the luminance value of the second image pickup signal is also not less than the predetermined threshold value, the photometric value signal selection section 51 is instructed to select the first photometric value signal instead of the second photometric value signal (steps S14 and S15).

That is, even when relatively intense and bright light is incident on only the image pickup device 23L once by the entrance of the forceps or the like, if the forceps or the like depart from the field of view range of the image pickup optical system 22L or the direction thereof is displaced so that the incidence of the relatively intense or bright light is released, the selection in the photometric value signal selection section 51 is returned to an initial state in the present embodiment.

Note that, if the luminance value of the first image pickup signal is not less than the predetermined threshold value and the luminance value of the second image pickup signal is also not less than the predetermined threshold value while the first photometric value signal is selected in the photometric value signal selection section 51, the control section 31 instructs the photometric value signal selection section 51 to maintain the selection of the first photometric value signal as it is (steps S14 and S15).

That is, if intense light is incident on not only the image pickup device 23L but also the image pickup device 23R, there is no great divergence in luminance value between the first image pickup signal and the second image pickup signal, and control of an exposure time is not significantly affected which of the first photometric value signal and the second photometric value signal is selected as the photometric value signal to be selected in the photometric value signal selection section 51. Thus, in the present embodiment, the first photometric value signal in an initial state is maintained in this case.

As described above, according to the first embodiment, there can be provided an endoscope system capable of maintaining accurate exposure control of image pickup signals even if a treatment instrument such as forceps enters a field of view range related to either one of left and right image pickup optical systems in a stereoscopic endoscope and relatively intense and bright light is incident on an image pickup section on the entrance side.

Second Embodiment

A second embodiment of the present invention will be described below. As described above, the above-described endoscope system according to the first embodiment presupposes that the luminance value (photometric value) of either one of the image pickup signals in the left and right image pickup sections in the stereoscopic endoscope is always selected to perform light adjustment control of the light source and selectively switches, if such relatively intense and bright light as to exceed the predetermined threshold value is incident by on either one of the left and right image pickup sections, the photometric value signal to be a basis of the light adjustment control of the light source to a photometric value signal related to the image pickup signal on the side other than the side on which the bright light is incident to maintain accurate exposure control of the image pickup signal.

On the other hand, an endoscope system according to the second embodiment performs light adjustment control of a light source based on a signal obtained by averaging luminance values (photometric values) of image pickup signals in both left and right image pickup sections in a stereoscopic endoscope.

Figure 6:
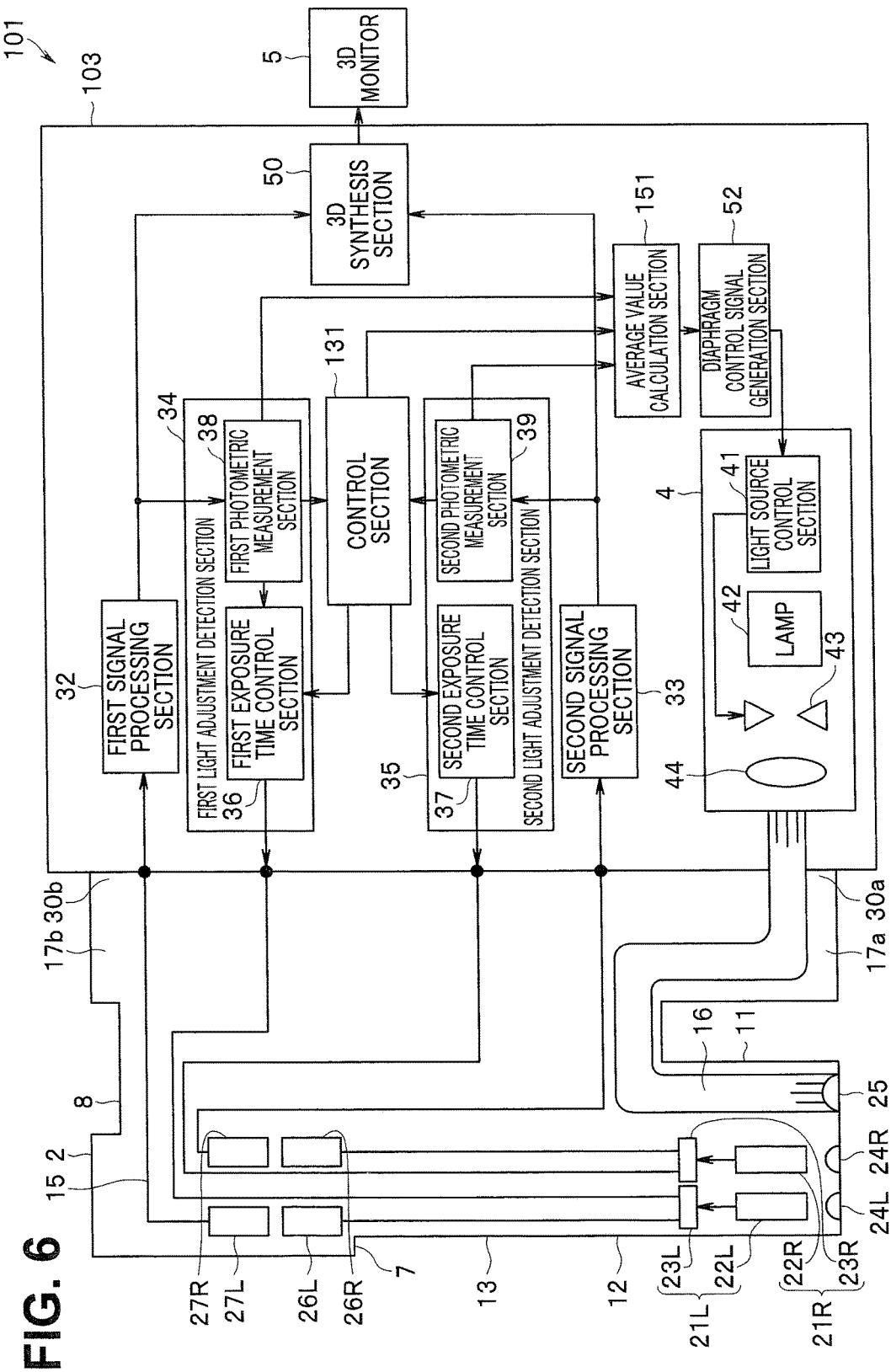
FIG. 6 is a diagram illustrating a configuration of an endoscope system according to a second embodiment of the present invention.

FIG. 6 is a diagram illustrating a configuration of the endoscope system according to the second embodiment of the present invention. As illustrated in FIG. 6, an endoscope system 101 according to the second embodiment is similar in its basic configuration to that in the first embodiment but mainly differs in that an average value calculation section 151 is provided instead of the photometric value signal selection section 51 in the first embodiment in a processor 103. Therefore, only a different part from that in the first embodiment is described, and description of a similar part to that in the first embodiment is omitted.

As described above, in the second embodiment, the processor 103 includes the average value calculation section 151 configured to calculate an average value of a first photometric value signal from a first photometric measurement section 38 and a second photometric value signal from a second photometric measurement section 39 under the control of a control section 131, and a diaphragm control signal generation section 52 configured to generate a diaphragm control signal in response to the average value of the first photometric value signal and the second photometric value signal calculated in the average value calculation section 151.

That is, in the second embodiment, a light source control section 41 controls a diaphragm 43 to control a light amount of illumination light based on the diaphragm control signal generated in response to the average value of the first photometric value signal and the second photometric value signal calculated in the average value calculation section 151.

Function of Second Embodiment

A function of the endoscope system according to the second embodiment will be described below.

Figure 7:
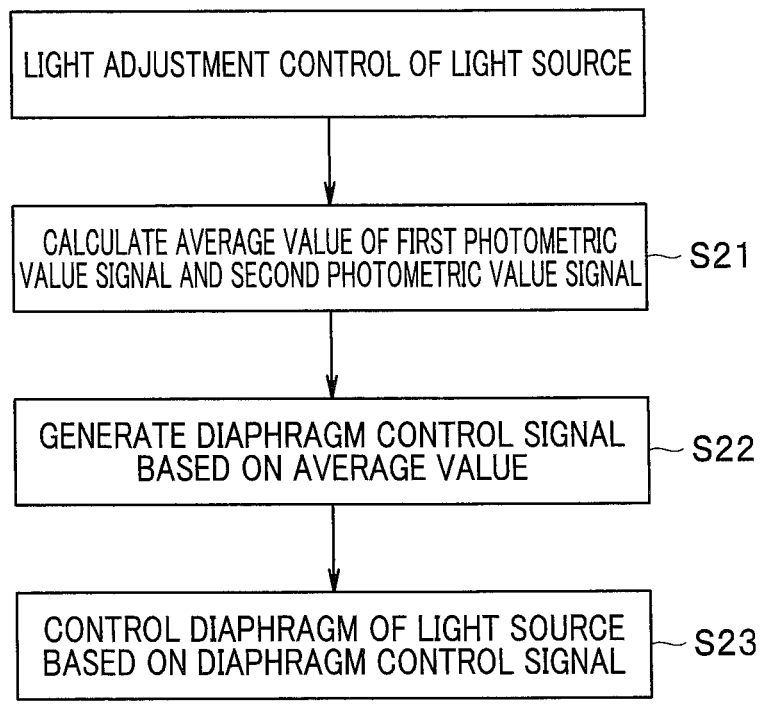
FIG. 7 is a flowchart illustrating light adjustment control of a light source in the case of a procedure in the endoscope system according to the second embodiment.

FIG. 7 is a flowchart illustrating the light adjustment control of the light source in the case of a procedure in the endoscope system according to the second embodiment.

When the control of the light source is started under the control of the control section 131 in the processor 103, the average value calculation section 151 calculates an average value of a first photometric value signal and a second photometric value signal under the control of the control section 131 in the processor 103 (step S21). Note that the average value can be calculated using known average value calculation such as a weighted average under a predetermined condition in addition to a simple average of the two photometric value signals.

The diaphragm control signal generation section 52 then generates a diaphragm control signal based on the average value (step S22), and the light source control section 41 in a light source section 4 controls the diaphragm 43 based on the diaphragm control signal, which has been generated in step S12, under the control of the control section 131 (step S23).

Thus, in the second embodiment, the diaphragm 43 of the light source is controlled based on the average value of the photometric value signals (the first photometric value signal and the second photometric value signal) related to respective image pickup signals from both left and right image pickup devices 23L and 23R. Therefore, even if relatively intense and bright light is incident because a treatment instrument such as forceps enters a field of view range related to either one of image pickup sections, for example, a rapid displacement of the diaphragm is relaxed. Thus, an effect on exposure control of the image pickup signal can be reduced.

As described above, according to the second embodiment, there can be provided an endoscope system capable of reducing an effect on exposure control of left and right image pickup signals by controlling a diaphragm of a light source based on an average value of photometric value signals related to the image pickup signals even if a treatment instrument such as forceps enters a field of view range related to either one of left and right image pickup optical systems in a stereoscopic endoscope and relatively intense and bright light is incident on an image pickup section on the entrance side.

Third Embodiment

A third embodiment of the present invention will be described below.

While an endoscope system according to the third embodiment is an endoscope system which performs image pickup using a stereoscopic endoscope 2, like in the second embodiment, a two-dimensional (2D) image can also be reproduced on a 3D monitor under a predetermined condition in addition to display of a 3D image on the 3D monitor.

Figure 8:
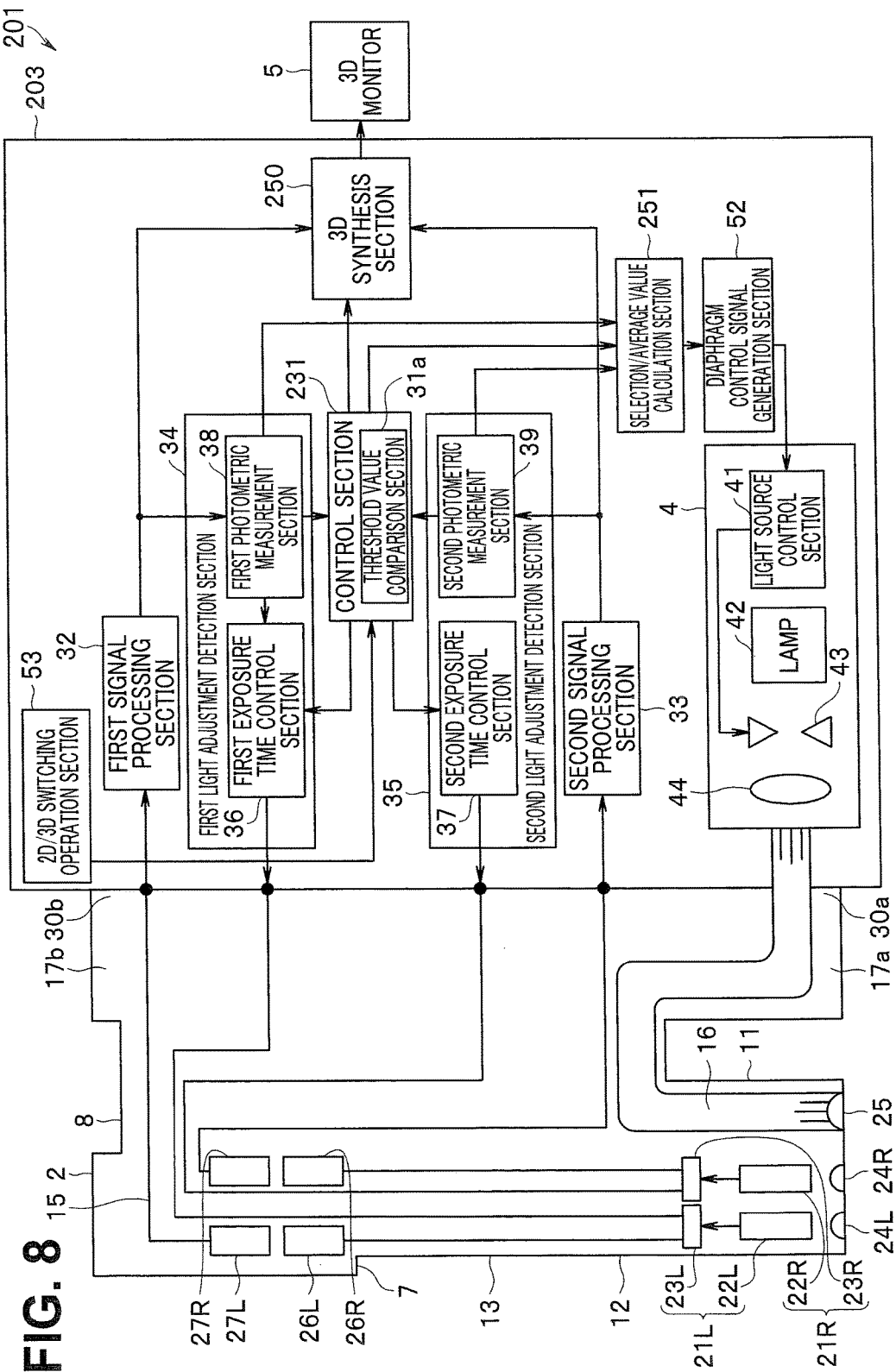
FIG. 8 is a diagram illustrating a configuration of an endoscope system according to a third embodiment of the present invention.

FIG. 8 is a diagram illustrating a configuration of the endoscope system according to the third embodiment of the present invention. An endoscope system 201 according to the third embodiment is similar in its basic configuration to that in the first embodiment but mainly differs in that a selection/average value calculation section 251 configured to select a photometric value signal and calculate an average value instead of the photometric value signal selection section 51 in the first embodiment in addition to providing a mechanism for switching between two dimensions (2D) and three dimensions (3D) in a processor 203. Therefore, only a different part from that in the first embodiment is described, and description of a similar part to that in the first embodiment is omitted.

As illustrated in FIG. 8, in the third embodiment, the processor 203 includes the selection/average value calculation section 251 having an average value calculation function of calculating an average value of a first photometric value signal from a first photometric measurement section 38 and a second photometric value signal from a second photometric measurement section 39 and a function of selecting either one of the first photometric value signal and the second photometric value signal under the control of a control section 231.

The processor 203 includes a 2D/3D switching operation section 53 configured to perform a switching operation between 2D and 3D.

Furthermore, the processor 203 includes a 3D synthesis section 250 configured to synthesize a first image pickup signal processed in a first signal processing section 32 and a second image pickup signal processed in a second signal processing section 33 to generate a predetermined 3D image signal while outputting the first image pickup signal outputted from the first signal processing section 32 as a 2D signal in response to an operation of the 2D/3D switching operation section 53 under the control of the control section 231.

In the present embodiment, the control section 231 confirms an operating state of the 2D/3D switching operation section 53, and issues an instruction, when a mode for outputting a 2D image signal is selected, to control the 3D synthesis section 250 to perform switching to output the first image pickup signal outputted from the first signal processing section 32 as a 2D signal while controlling the selection/average value calculation section 251 to perform switching to set the mode to a mode for selecting the first photometric value signal.

On the other hand, the control section 231 confirms the operating state of the 2D/3D switching operation section 53, and issues an instruction, when a mode for outputting a 3D image signal is selected, to control the 3D synthesis section 250 to perform switching to perform the above-described 3D synthesis processing while controlling the selection/average value calculation section 251 to perform switching to set the mode to a mode for calculating an average value of the first photometric value signal and the second photometric value signal, like in the second embodiment.

Function of Third Embodiment

A function of the endoscope system according to the third embodiment will be described below.

Figure 9:
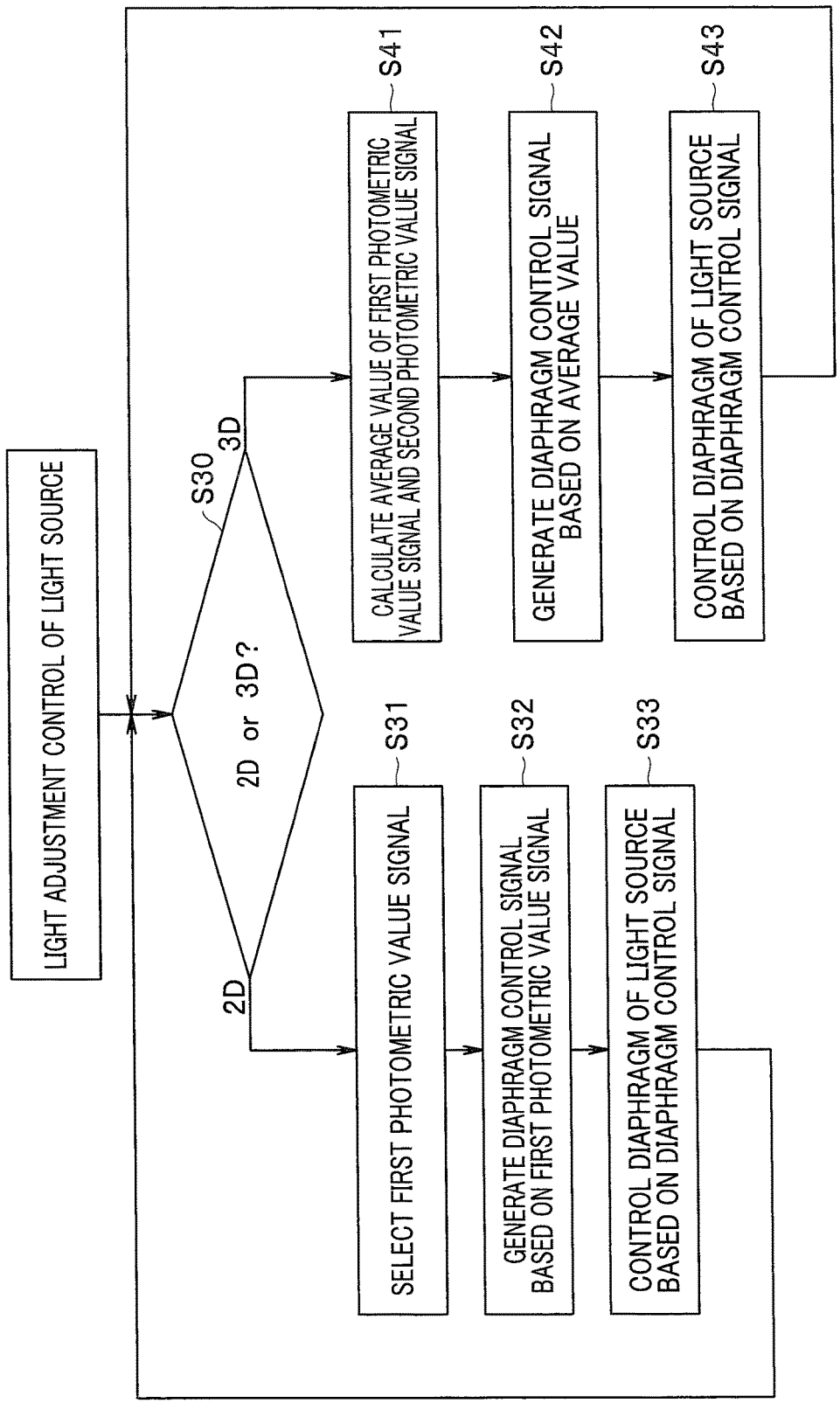
FIG. 9 is a flowchart illustrating light adjustment control of a light source in the case of a procedure in the endoscope system according to the third embodiment.

FIG. 9 is a flowchart illustrating light adjustment control of a light source in the case of a procedure in the endoscope system according to the third embodiment.

When the control of the light source is started under the control of the control section 231 in the processor 203, it is first determined which of a 2D image signal output mode and a 3D image signal output mode is selected in the 2D/3D switching operation section 53 (step S30).

Then, if the 2D image signal output mode is selected, the selection/average value calculation section 251 selects a first photometric value signal under the control of the control section 231 (step S31). A diaphragm control signal generation section 52 then generates a diaphragm control signal based on the first photometric value signal (step S32). A light source control section 41 in a light source section 4 controls a diaphragm 43 based on the diaphragm control signal, which has been generated in step S32, under the control of the control section 231 (step S33), and the processing returns to step S30.

On the other hand, if the 3D image signal output mode is selected in step S30, described above, the selection/average value calculation section 251 calculates an average value of the first photometric value signal and a second photometric value signal under the control of the control section 231 (step S41).

The diaphragm control signal generation section 52 then generates a diaphragm control signal based on the average value (step S42). The light source control section 41 in the light source section 4 controls the diaphragm 43 based on the diaphragm control signal, which has been generated in step S42, under the control of the control section 231 (step S43), and the processing returns to step S30, like in the second embodiment.

Thus, in the third embodiment, when the 3D image signal output mode is selected, the diaphragm 43 of the light source is controlled based on the average value of the photometric value signals (the first photometric value signal and the second photometric value signal) related to the respective image pickup signals from both the left and right image pickup devices 23L and 23R, like in the second embodiment, to produce a similar effect to that produced in the second embodiment.

As described above, the endoscope system according to the third embodiment enables reproduction of the 2D image on the 3D monitor when the 2D image signal output mode is selected, although a similar effect to that produced in the second embodiment is produced when the 3D image signal output mode is selected.

While the first image pickup signal outputted from the first signal processing section 32 is outputted as the 2D image signal in the 3D synthesis section 250 when a mode for outputting the 2D image signal is selected in the third embodiment, the present invention is not limited to this. For example, the second image pickup signal outputted from the second signal processing section 33 may be outputted as the 2D image signal.

Fourth Embodiment

A fourth embodiment of the present invention will be described below.

While an endoscope system according to the fourth embodiment is an endoscope system which performs image pickup using a stereoscopic endoscope 2, like in the first and second embodiments, light adjustment control of a light source is generally performed in response to a photometric value signal related to an image pickup signal in either one of left and right image pickup sections, and is performed based on an average value of a first photometric value signal and a second photometric value signal when a treatment instrument such as forceps enters a field of view range related to either one of left and right image pickup optical systems and relatively intense and bright light is incident on the image pickup section on the entrance side, like in the second embodiment.

Figure 10:
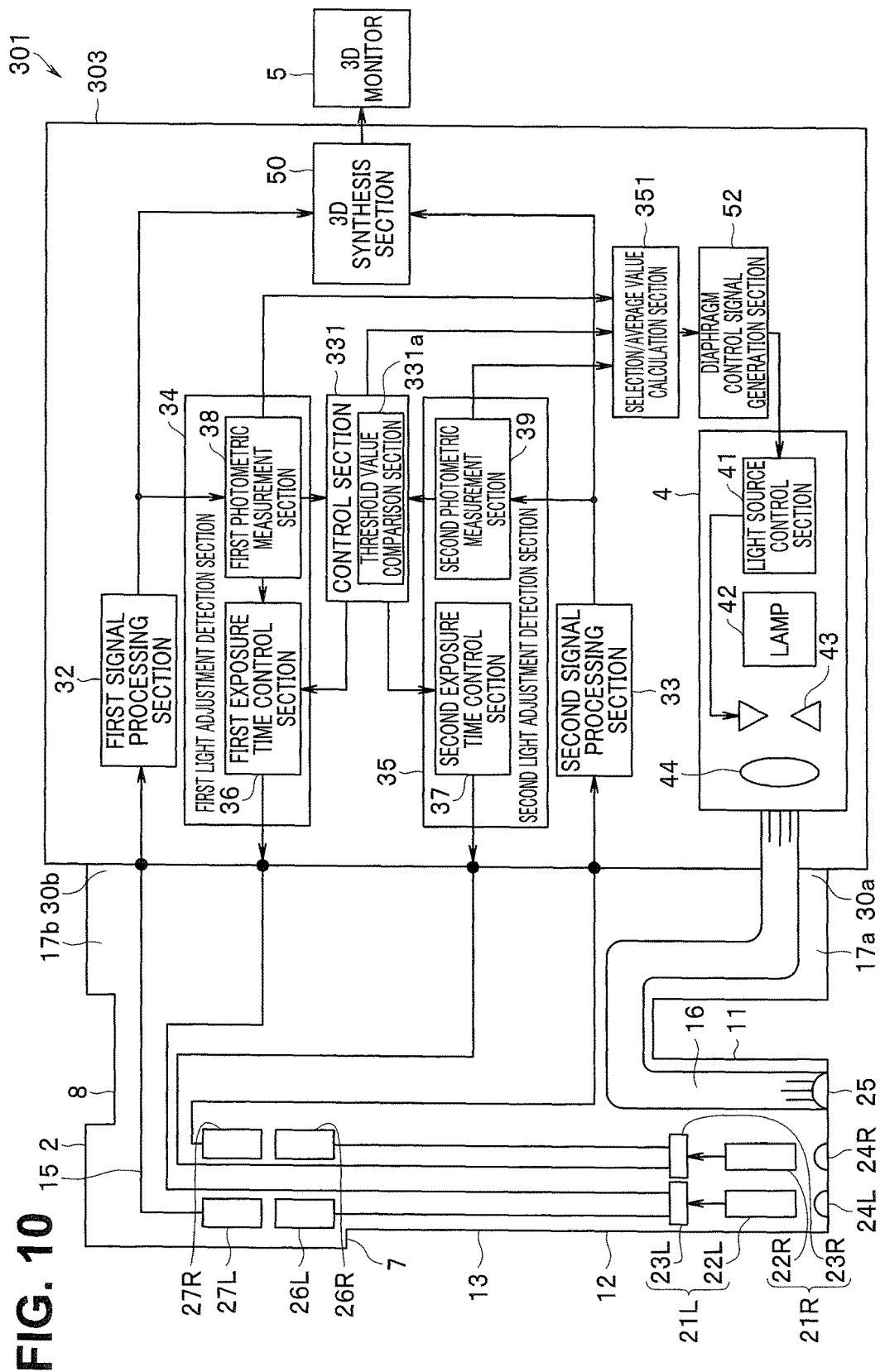
FIG. 10 is a diagram illustrating a configuration of an endoscope system according to a fourth embodiment of the present invention.

FIG. 10 is a diagram illustrating a configuration of the endoscope system according to the fourth embodiment of the present invention. An endoscope system 301 according to the fourth embodiment is similar in its basic configuration to that in the first embodiment but differs in that a processor 303 includes a selection/average value calculation section 351 configured to select whether the light adjustment control is performed based on either one of the photometric value signals or is performed based on an average value of both the photometric value signals instead of the photometric value signal selection section 51 in the first embodiment. Therefore, only a different part from that in the first embodiment is described, and description of a similar part to that in the first embodiment is omitted.

As illustrated in FIG. 10, in the fourth embodiment, the processor 303 includes the selection/average value calculation section 351 having an average value calculation function of calculating an average value of a first photometric value signal from a first photometric measurement section 38 and a second photometric value signal from a second photometric measurement section 39 and a function of selecting either one of the first photometric value signal and the second photometric value signal under the control of a control section 331.

The control section 331 in the present embodiment includes a threshold value comparison section 331a configured to compare a luminance value of a first image pickup signal or a second image pickup signal processed in a first signal processing section 32 or a second signal processing section 33 with a predetermined threshold value.

Function of Fourth Embodiment

A function of the endoscope system according to the fourth embodiment will be described below.

Figure 11:
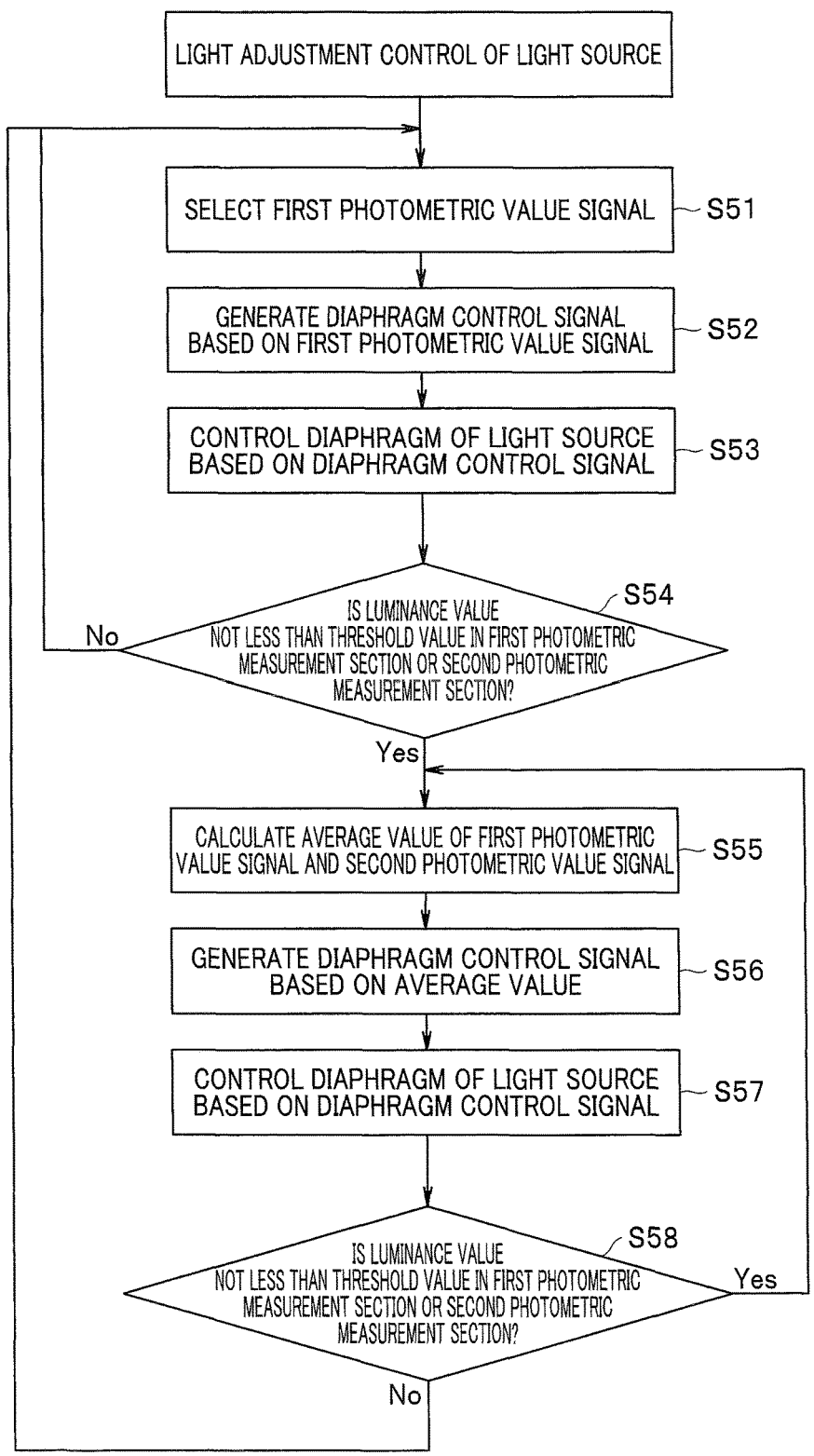
FIG. 11 is a flowchart illustrating light adjustment control of a light source in the case of a procedure in the endoscope system according to the fourth embodiment.

FIG. 11 is a flowchart illustrating the light adjustment control of the light source in the case of a procedure in the endoscope system according to the fourth embodiment.

When the control of the light source is started under the control of the control section 331 in the processor 303, the selection/average value calculation section 351 selects a first photometric value signal under the control of the control section 331 (step S51). A diaphragm control signal generation section 52 then generates a diaphragm control signal based on the first photometric value signal (step S52). A light source control section 41 in a light source section 4 controls a diaphragm 43 based on the diaphragm control signal, which has been generated in step S52, under the control of the control section 331 (step S53).

As the first embodiment below, the first photometric measurement section 38 in a first light adjustment detection section 34 and the second photometric measurement section 39 in a second light adjustment detection section 35 respectively photometrically measure the luminance value of the first image pickup signal and the luminance value of the second image pickup signal under the control of the control section 331.

The threshold value comparison section 331a in the control section 331 then compares the luminance value of the first image pickup signal and the luminance value of the second image pickup signal with a predetermined threshold value, and determines whether either one of the luminance value of the first image pickup signal and the luminance value of the second image pickup signal is not less than the threshold value (step S54).

If neither the respective luminance values of the first image pickup signal nor the second image pickup signal reach not less than the threshold value in step S54, the processing returns to step S51. In step S51, the control section 331 controls the selection/average value calculation section 351, the diaphragm control signal generation section 52, and the light source control section 41 so that the control of the diaphragm 43 based on the first photometric value signal is continued.

If the threshold value comparison section 331a determines that either one of the luminance value of the first image pickup signal and the luminance value of the second image pickup signal is not less than the threshold value in step S54, described above, the selection/average value calculation section 351 calculates an average value of the first photometric value signal and the second photometric value signal under the control of the control section 331 (step S55).

The diaphragm control signal generation section 52 then generates a diaphragm control signal based on the average value (step S56), like in the second embodiment. The light source control section 41 in the light source section 4 controls the diaphragm 43 based on the diaphragm control signal, which has been generated in step S56, under the control of the control section 331 (step S57).

Then, the threshold value comparison section 331a in the control section 331 compares the luminance value of the first image pickup signal and the luminance value of the second image pickup signal with the predetermined threshold value again, and determines whether either one of the luminance values of the first image pickup signal and the second image pickup signal is not less than the threshold value (step S58).

As long as either one of the respective luminance values of the first image pickup signal and the second image pickup signal is not less than the threshold value in step S58, the processing returns to step S55. In step S55, the light adjustment control of the light source based on the average value of the first photometric value signal and the second photometric value signal is continued. On the other hand, if both the luminance values of the first image pickup signal and the second image pickup signal reach less than the threshold value, the processing returns to step S51. In step S51, the light adjustment control of the light source based on the first photometric value signal is performed.

Thus, in the fourth embodiment, the light adjustment control of the light source is generally performed in response to the photometric value signal related to the image pickup signal in either one of the left and right image pickup sections. However, when the treatment instrument such as the forceps enters the field of view range related to either one of the left and right image pickup optical systems, and relatively intense and bright light is incident on the image pickup section on the entrance side, a similar effect to that produced in the second embodiment can be produced by performing the light adjustment control of the light source based on the average value of the first photometric value signal and the second photometric value signal, like in the second embodiment.

Note that the present invention is not limited to the above-described embodiments themselves, and can be embodied by deforming components without departing from the spirit of the invention in an implementation stage. Various aspects of the invention can be formed by combining a plurality of components disclosed in the above-described embodiments, as needed. For example, some of all the components described in the embodiments may be deleted. Further, components over different embodiments may be combined, as needed.

What is claimed is:

1. An image pickup system comprising:
   a light source configured to irradiate an object with illumination light;
   a first image pickup section including a first image pickup device capable of picking up an optical image of the object and outputting the optical image as a first image pickup signal;
   a second image pickup section including a second image pickup device capable of picking up the optical image of the object and outputting the optical image as a second image pickup signal having a parallax from the first image pickup signal;
   a first photometric measurement section configured to detect a brightness of an object image as a first photometric value for the first image pickup signal;
   a second photometric measurement section configured to detect a brightness of the object image as a second photometric value for the second image pickup signal;
   a first exposure time control section configured to control an exposure time of the first image pickup signal based on the first photometric value;
   a second exposure time control section configured to control an exposure time of the second image pickup signal based on the second photometric value;
   an exposure control section configured to control at least one of the first exposure time control section and the second exposure time control section so that the brightness of the object image for the first image pickup signal and the brightness of the object image for the second image pickup signal become equal to each other;
   a photometric value selection section configured to select either one of the first photometric value detected in the first photometric measurement section and the second photometric value detected in the second photometric measurement section; and
   a light amount control section configured to control a light amount of the illumination light irradiated from the light source based on the first photometric value or the second photometric value selected by the photometric value selection section.

2. The image pickup system according to claim 1, further comprising
   an average value calculation section configured to subject the first photometric value detected in the first photometric measurement section and the second photometric value detected in the second photometric measurement section to predetermined average processing to calculate an average photometric value,
   wherein the light amount control section controls the light amount of the illumination light irradiated from the light source based on the first photometric value or the second photometric value selected by the photometric value selection section, or the average photometric value calculated in the average value calculation section.

3. The image pickup system according to claim 2, wherein the light amount control section controls the light amount of the illumination light irradiated from the light source based on the first photometric value or the second photometric value selected by the photometric value selection section in a first state, and controls the light amount of the illumination light irradiated from the light source based on the average photometric value calculated in the average value calculation section when a second state is reached based on a detection result in the first photometric measurement section or the second photometric measurement section.

4. The image pickup system according to claim 2, further comprising an image signal selection section configured to select either one of a 2D image signal generated using either one of the first image pickup signal and the second image pickup signal and a 3D image signal generated by synthesizing the first image pickup signal and the second image pickup signal and display the selected image signal.

5. The image pickup system according to claim 4, wherein, when the image signal selection section selects the 3D image signal, the light amount control section controls the light amount of the illumination light irradiated from the light source based on the average photometric value calculated in the average value calculation section.

6. The image pickup system according to claim 4, wherein, when the image signal selection section selects the 2D image signal, the light amount control section controls the light amount of the illumination light irradiated from the light source based on either one of the first photometric value and the second photometric value to correspond to the generation of the 2D image signal using the first image pickup signal or the second image pickup signal.

* * * * *